US010692355B2

(12) United States Patent
Waghode et al.

(10) Patent No.: US 10,692,355 B2
(45) Date of Patent: Jun. 23, 2020

(54) SYSTEM AND METHOD FOR EFFICIENTLY MONITORING HAND HYGIENE

(71) Applicant: Cognizant Technology Solutions India Pvt. Ltd., Chennai (IN)

(72) Inventors: Nitesh Dattu Waghode, Pune (IN); Vivek Vasant Diwanji, Pune (IN); Amit Bindumadhav Pingle, Pune (IN); Himanshu Pradhan, Gwalior (IN); Mandar Pandurang Patil, Pune (IN); Aman Singhal, Dehradun (IN); Ashish Sharma, Dist-Mahoba (IN)

(73) Assignee: COGNIZANT TECHNOLOGY SOLUTIONS INDIA PVT. LTD., Chennai (IN)

( * ) Notice: Subject to any disclaimer, the term of this patent is extended or adjusted under 35 U.S.C. 154(b) by 0 days.

(21) Appl. No.: 16/197,782

(22) Filed: Nov. 21, 2018

(65) Prior Publication Data

US 2020/0074835 A1    Mar. 5, 2020

(30) Foreign Application Priority Data

Sep. 4, 2018    (IN) .............................. 201841033184

(51) Int. Cl.
*G08B 21/24*   (2006.01)
*G16H 40/20*   (2018.01)

(52) U.S. Cl.
CPC ........... *G08B 21/245* (2013.01); *G16H 40/20* (2018.01)

(58) Field of Classification Search
CPC ................................................... G08B 21/245
See application file for complete search history.

(56) References Cited

U.S. PATENT DOCUMENTS

| 8,237,558 | B2 | 8/2012 | Momen | |
|---|---|---|---|---|
| 10,078,956 | B1 * | 9/2018 | Kusens | ................ G08B 21/245 |
| 2010/0321180 | A1 * | 12/2010 | Dempsey | ............... G06Q 10/06 340/539.12 |
| 2011/0169646 | A1 | 7/2011 | Raichman | |

\* cited by examiner

*Primary Examiner* — Omeed Alizada
(74) *Attorney, Agent, or Firm* — Cantor Colburn LLP

(57) ABSTRACT

A system and computer-implemented method for efficiently monitoring hand hygiene is provided. The system comprises one or more sensors configured to determine presence of one or more individuals in vicinity. The system further comprises one or more controllers configured to ascertain identity of the one or more individuals. The one or more controllers are further configured to send one or more alerts to the one or more identified individuals to wash their hands. Furthermore, the one or more controllers are configured to monitor one or more handwashing instances by the one or more identified individuals and generate one or more compliance results for each of the one or more monitored handwashing instances. The one or more controllers are also configured to initiate one or more actions corresponding to each of the one or more monitored handwashing instances based on the generated one or more compliance results.

16 Claims, 3 Drawing Sheets

SYSTEM AND METHOD FOR EFFICIENTLY MONITORING HAND HYGIENE

CROSS REFERENCE TO RELATED APPLICATION

This application is related to and claims the benefit of Indian Patent Application Number 201841033184 filed on Sep. 4, 2018, the contents of which are herein incorporated by reference in their entirety.

FIELD OF THE INVENTION

The present invention relates generally to hand hygiene. More particularly, the present invention provides a system and method for efficiently monitoring hand hygiene.

BACKGROUND OF THE INVENTION

Hand hygiene is defined as any method that removes dirt and microorganisms on hands. Hand hygiene is the most important and basic means of reducing the spread of infections. Therefore, it is imperative that facilities such as healthcare, schools, food processing, restaurants etc. ensure effective hand hygiene in order to reduce hygiene and healthcare associated infections.

Conventionally, various systems and methods exist for monitoring hand hygiene. For example, measuring hand wash product consumption pattern and manual staff monitoring to determine adherence to hand hygiene. Also, there are several technology assisted direct observation and monitoring solutions available that are employed to monitor hand hygiene. However, the above-mentioned systems and methods suffer from several disadvantages. These systems and methods do not provide a mechanism to identify individuals that do not comply with hand hygiene guidelines. Further, the abovementioned system and method are unable to determine the effectiveness of a particular handwashing instance. Furthermore, the above-mentioned systems and methods do not provide real-time monitoring and reporting of hand hygiene compliance and therefore do not provide any opportunity to inform the individual in case of improper handwashing. Due to the aforementioned disadvantages, these systems and methods are unreliable, inconsistent, ineffective and time-consuming.

In light of the above-mentioned disadvantages, there is a need for a system and method for efficiently monitoring hand hygiene. Further, there is a need for system and method that is capable of identifying individuals and determining effectiveness of each and every handwashing instance. Furthermore, there is a need for a system and method that is capable of real-time monitoring and reporting of hand hygiene compliance. Also, there is a need for a system and method that is reliable, cost efficient, consistent and facilitates organizations and individuals to efficiently implement and comply with hand hygiene guidelines.

SUMMARY OF THE INVENTION

A system and computer-implemented method for efficiently monitoring hand hygiene is provided. The system comprises one or more sensors configured to determine presence of one or more individuals in vicinity. The system further comprises one or more controllers configured to ascertain identity of the one or more individuals. The one or more controllers further configured to send one or more alerts to the one or more identified individuals to wash their hands. Furthermore, the one or more controllers configured to monitor one or more handwashing instances by the one or more identified individuals and generate one or more compliance results for each of the one or more monitored handwashing instances. The one or more controllers are also configured to initiate one or more actions corresponding to each of the one or more monitored handwashing instances based on the generated one or more compliance results.

In an embodiment of the present invention, the one or more sensors comprise cameras, beacons, Radio-Frequency Identification (RFID) readers, proximity sensors, movement sensors, audio sensors, light sensors, activity sensors, motion sensors and olfactory sensors. In an embodiment of the present invention, the presence of the one or more individuals in vicinity of the one or more sensors is determined by tracking one or more user devices of the one or more individuals.

In an embodiment of the present invention, the one or more user devices are electronic communication devices comprising mobile phones, tablets and wearable devices. Further, the wearable devices comprise smart watches, smart glasses, smart bands and fitness bands. In an embodiment of the present invention, the one or more alerts are notifications comprising a haptic motion, an audio notification and a visual notification.

In an embodiment of the present invention, the one or more handwashing instances are monitored using one or more motion sensing technologies comprising an accelerometer, a gyroscope, a magnetometer and a camera. In an embodiment of the present invention, the one or more compliance results comprise information which indicates whether the one or more identified individuals complied with handwashing guidelines during the one or more handwashing instances. Further, the handwashing guidelines are a set of minimum requirements with respect to pattern, sequence, timing and energy used during washing for complete hand hygiene and further wherein the handwashing guidelines are configurable based on requirement.

In an embodiment of the present invention, the one or more actions corresponding to each of the one or more monitored handwashing instances comprise sending the one or more generated compliance results to at least one of: one or more user devices, one or more dispensers, a cloud platform, a server, a web application, an edge computing platform, a fog computing platform and an Internet of Things (IoT) platform. In an embodiment of the present invention, the compliance results comprise data related to washing liquid and chemical levels, dispenser condition and status of sensors and controllers. In an embodiment of the present invention, the one or more compliance results are analyzed to generate insights comprising information related to least and most non-compliant individuals, gamification, dispenser and controller diagnostics, dispenser refilling prediction and most and least compliant zones and places.

In an embodiment of the present invention, the system further comprises a gamification module configured to provide gamification elements comprising individual scores, leaderboards, rankings, incentive models and compliance percentages using the one or more compliance results.

The computer-implemented method for efficiently monitoring hand hygiene, via program instructions stored in a memory and executed by a processor, comprises determining presence of one or more individuals in vicinity of one or more sensors. The computer-implemented method further comprises ascertaining identity of the one or more individuals. Furthermore, the computer-implemented method comprises sending one or more alerts to the one or more identified individuals to wash their hands. Also, the computer-implemented method comprises monitoring one or more handwashing instances by the one or more identified individuals. In addition, the computer-implemented method comprises generating one or more compliance results for each of the one or more monitored handwashing instances. The computer-implemented method further comprises initiating one or more actions corresponding to each of the one or more monitored handwashing instances based on the generated one or more compliance results.

BRIEF DESCRIPTION OF THE ACCOMPANYING DRAWINGS

The present invention is described by way of embodiments illustrated in the accompanying drawings wherein.

DETAILED DESCRIPTION OF THE INVENTION

A system and method for efficiently monitoring hand hygiene is described herein. The invention provides a system and method that is capable of identifying individuals and determining effectiveness of each and every handwashing instance. The invention further provides a system and method that is capable of real-time monitoring and reporting of hand hygiene compliance. Furthermore, the invention provides a system and method that is reliable, cost efficient, consistent and facilitates organizations and individuals to efficiently implement and comply with hand hygiene guidelines.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention would now be discussed in context of embodiments as illustrated in the accompanying drawings.

Figure 1:
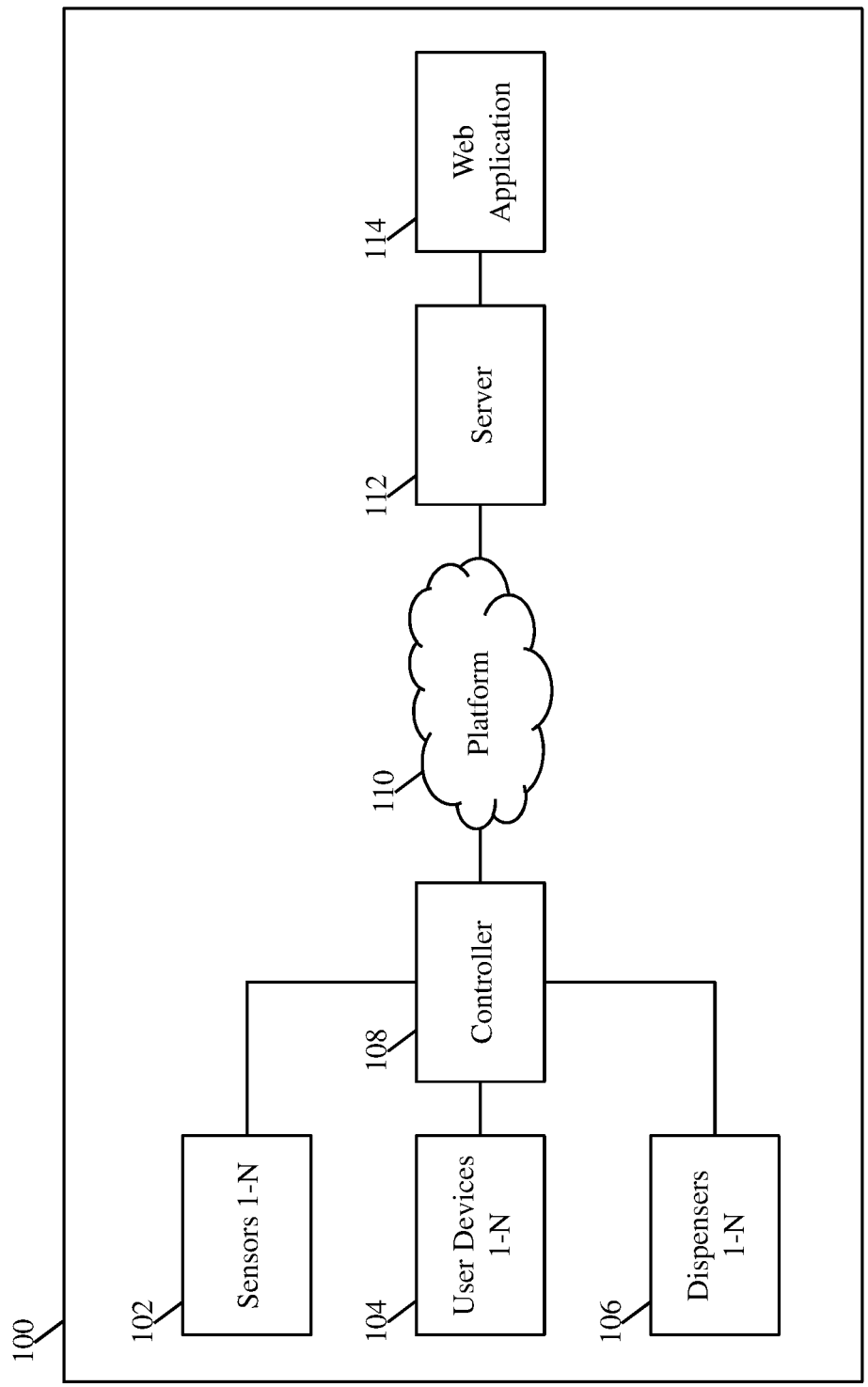
FIG. 1 is a block diagram illustrating a system for efficiently monitoring hand hygiene, in accordance with an embodiment of the present invention.

FIG. 1 is a block diagram illustrating a system for efficiently monitoring hand hygiene, in accordance with an embodiment of the present invention. The system 100 comprises one or more sensors 102, one or more user devices 104, one or more dispensers 106, one or more controllers 108, one or more platforms 110, one or more servers 112 and a web application 114.

The one or more sensors 102 are configured to determine presence of one or more individuals in its vicinity. The one or more sensors 102 include, but not limited to, cameras, beacons, Radio-Frequency Identification (RFID) readers, proximity sensors, movement sensors, audio sensors, light sensors, activity sensors, motion sensors and olfactory sensors. Further, the one or more sensors 102 employ technologies such as, but not limited to, Bluetooth, Infrared and Zigbee. In an embodiment of the present invention, the one or more sensors 102 are mounted at entry/exit or at any suitable place inside or outside of various pre-defined zones within a pre-defined region such as, but not limited to, a healthcare facility, a kitchen, a restaurant, a food packaging unit, a food processing unit, a school, a cafeteria, a house and any other region that requires monitoring of hand hygiene of the one or more individuals. In an exemplary embodiment of the present invention, the one or more sensors 102 are mounted on doors of the patient rooms in a hospital. In an embodiment of the present invention, the one or more individuals include, but not limited to, guests, hospital personnel, food processing workers, cooking staff, school staff, restroom workers and users, pharmaceutical room cleaning workers and any person within the pre-defined region.

In an embodiment of the present invention, the one or more sensors 102 determine presence of the one or more individuals by tracking the one or more user devices 104 of the one or more individuals. In an embodiment of the present invention, the one or more user devices 104 are tracked using different types of data and signals such as, but not limited to, sensing and communication signals, electromagnetic features (such as phase and frequency), antenna IDs, tag IDs, light signatures, audio signatures and heat signatures. In an embodiment of the present invention, Received Signal Strength Indicator (RSSI) values received from the one or more user devices 104 are used to determine presence of the one or more individuals. The one or more user devices 104 are electronic communication devices such as, but not limited to, mobile phones, tablets and wearable devices. In an embodiment of the present invention, the wearable devices include, but not limited, smart watches, smart glasses, smart bands and fitness bands. In an embodiment of the present invention, the one or more user devices 104 are specially designed proprietary wearable devices worn by the one or more individuals for hand hygiene monitoring. In an embodiment of the present invention, the one or more user devices 104 include, but not limited to, an RFID tag which is tracked by the RFID reader to determine presence of the individual in the vicinity of the RFID reader. In an embodiment of the present invention, the one or more user devices 104 comprise motion sensing technologies such as, but not limited to, gyroscope, accelerometer, magnetometer and camera that facilitate in determining hand washing patterns of the individuals for monitoring hand hygiene.

In an embodiment of the present invention, on determining the presence of the one or more individuals, the one or more sensors 102 ascertain identity of the one or more individuals using their user devices 104. In another embodiment of the present invention, on determining the presence of the one or more individuals, the one or more sensors 102 send one or more triggers to the one or more controllers 108. On receiving the one or more triggers, the one or more controllers 108 facilitate ascertaining the identity of the one or more individuals using the one or more user devices 104 present in the vicinity of the one or more sensors 102 that belong to the one or more individuals. The one or more controllers 108 may comprise a database of registered user devices belonging to various individuals. In an embodiment of the present invention, the one or more triggers for communication and assessment include, but not limited to, device details, user identification data, time-stamps, location information and dispenser data. The identification data is matched with entries in a pre-stored list of individuals/user devices and corresponding pre-stored identification data in the database of the registered individuals/user devices to ascertain the identity of the individual/user device. In another embodiment of the present invention, the identification data is used for automatic registration at run time in case of absence of a corresponding pre-stored identification data. In an embodiment of the present invention, determination of identity of the individual/user device may happen locally at, but not limited to, the one or more sensors 102, the one or more user devices 104, the one or more dispensers 106, the one or more controllers 108, one or more gateways, one or more processors and one or more servers or a combination thereof.

In an embodiment of the present invention, determination of identity of the individual/user device may happen globally at, but not limited to, an Internet of Things (IoT) platform, a cloud platform, an edge computing platform, a fog computing platform, the server 112 or a combination thereof. The determination of the identity of the individual/user device may involve security measures such as, but not limited to, token passing and usage of public/private keys. In an embodiment of the present invention, the user devices 104 are strictly associated to an individual user. In another embodiment of the present invention, a particular user device 104 may be shared by multiple users with a tracking functionality or mechanism defining the current individual using the user device 104.

In an embodiment of the present invention, the system 100 is capable of determining whether or not the individual is registered. For example, in a healthcare setting such as a hospital, the system 100 is capable of determining if the individual present in the vicinity of the one or more sensors 102 is a healthcare worker or a guest visiting a patient. In an embodiment of the present invention, identification of the one or more individual is not mandatory and the system 100 is capable of monitoring hand hygiene compliance irrespective of the identity of the individual.

In an exemplary embodiment of the present invention, an individual may have two or more user devices 104 such as a mobile phone and a wearable device. Further, the mobile phone and the wearable device communicate with each other via a hand hygiene application, installed on the mobile phone and/or the wearable device, using any appropriate short range and/or long range communication protocols such as, but not limited to, Bluetooth, ultra-wideband, ZigBee, LoRa technology—and Wi-Fi. In an embodiment of the present invention, the location of the one or more individuals is tracked via their mobile phone or any Commercial-Of-The-Shelf (COTS) device using location tracking technologies such as, but not limited to, Global Positioning System (GPS), WiFI, camera and inertial sensors. Further, the one or more individuals are notified to wash their hands via their mobile phone. Furthermore, the mobile phone via the hand hygiene application is capable of identifying the individual, recording hand washing instances using the camera of the individual's mobile phone and forwarding the handwashing instances to at least one of the controller 108, the server, the cloud platform and the IoT platform in real-time for monitoring.

In an embodiment of the present invention, once the identity of the one or more individuals is determined, one or more alerts are sent to the one or more identified individuals to wash their hands. In an embodiment of the present invention, the one or more alerts are sent to at least one of: the one or more user devices 104 of the one or more individuals and to the server 112 for storing. In an embodiment of the present invention, the one or more alerts are stored as, but not limited to, one or more log files or within a database using a structured or an unstructured format such as key/value pairs. Further, the hand hygiene application is installed on the user device 104 which facilitates communication and receives the one or more alerts from the one or more controllers 108. In an embodiment of the present invention, the wearable device receives the one or more alerts from the one or more controllers 108 and is configured to provide notifications in the form of, but not limited to, haptic motion, audio and visual notifications in order to alert the individual to wash his/her hands.

In an embodiment of the present invention, the one or more controllers 108 communicate with the one or more dispensers 106 and turn on a light or initiate blinking of a light on systems such as, but not limited to, the one or more user devices 104 and the one or more dispensers 106 to alert the one or more individuals in the vicinity of the one or more sensors 102 to wash their hands. In another embodiment of the present invention, the one or more dispensers 106 initiate an audio alert or a visual alert or both and automatically dispense hand washing product if the one or more individuals are standing near the dispenser 106. In case the one or more individuals are away from the one or more dispensers then the one or more individuals are notified to wash their hands. In yet another embodiment of the present invention, the sensor 102 is mounted on the dispenser 106. In yet another embodiment of the present invention, the dispenser 106 is capable of performing functionalities of the sensor 102 as well. In yet another embodiment of the present invention, the one or more controllers 108 have the one or more sensors 102 installed within them. Further, the one or more sensors 102 may be stationary or movable or installed on a movable platform. In an embodiment of the present invention, the movable platform is a robot.

In an embodiment of the present invention, the one or more dispensers 106, using a camera, take a picture or video, record and monitor one or more hand washing instances by the one or more identified individuals. Further, the camera can also be used for identifying the person using face recognition prior to monitoring hand washing. Furthermore, the camera may be installed in any predefined region or near the dispenser or above the dispenser. In another embodiment of the present invention, the one or more dispensers 106 record and monitor the one or more handwashing instances using one or more motion recognition technologies such as, but not limited to, accelerometer, gyroscope, magnetometer and camera. In yet another embodiment of the present invention, on receiving the one or more alerts to wash their hands, the one or more individuals access the hand hygiene application on their mobile phone or personal computing device or Personal Digital Assistant (PDA) or wearable device which then monitors the one or more hand washing instances by the one or more identified individuals. In yet another embodiment of the present invention, the one or more handwashing instances are monitored using the one or more motion sensing technologies such as, but not limited to, accelerometer, gyroscope, magnetometer and camera residing on, but not limited to, the wearable device worn by the one or more identified individuals.

The one or more controllers 108 receive data related to the monitoring of the one or more handwashing instances from at least one of: the one or more sensors 102, the one or more user devices 104 and the one or more dispensers 106 and generate one or more compliance results for each of the one or more monitored handwashing instances. The one or more compliance results include, but not limited to, information which indicates whether the one or more identified individuals complied with hand washing guidelines during the one or more handwashing instances. The handwashing guidelines are a set of minimum requirements with respect to but not limited to pattern, sequence, timing (which includes total and atomic/sub patterns) and energy used during washing for complete hand hygiene. Further, the handwashing guidelines are configurable and pre-defined in the system 100. Furthermore, the handwashing guidelines are defined and configured as per requirement of the application. In an embodiment of the present invention, the compliance results also comprise data related to, but not limited to, washing liquid and chemical levels, dispenser condition status of sensors and controllers and conditions for the purpose of maintaining the hygiene ecosystem.

In an embodiment of the present invention, the one or more controllers 108 comprise a sensing and computing application which uses a combination of various algorithms and techniques such as, but not limited to, time-series pattern matching and event detection algorithms, Dynamic Time Warping (DTW) algorithms, different distance metrics, clustering and correlation techniques and spectral techniques such as discrete Fourier transform for energy computation, key metric computation and classifying patterns into different categories or buckets thereby determining if the one or more identified individuals complied with the hand hygiene guidelines during the one or more monitored handwashing instances. The one or more controllers 108 are trained using various handwashing samples prior to deployment of the system 100 and/or during run time. Further, the one or more controllers 108 can be trained using edge computing, fog computing or cloud based training with over the air update or deployment to controllers. Furthermore, the handwashing samples are stored in a pattern library within the controller 108. In another embodiment of the present invention, the system 100 is trained using different self-learning techniques or human driven training algorithms. The handwashing samples include different types of handwashing patterns and sequences that either comply or do not comply with the handwashing guidelines. In an embodiment of the present invention, the samples used for training the one or more controllers 108 include, but not limited to, handwashing patterns adhering to World Health Organization (WHO) hand hygiene guidelines or any other guidelines or a combination thereof. Further, the system 100 is flexible to handle any hand washing guidelines or combination thereof. In an embodiment of the present invention, the handwashing samples are categorized into predefined categories or buckets such as, but not limited to, vigorous, normal and slow based on predefined threshold values of one or more features such as, but not limited to, energy and root mean square. Further, categorization of the handwashing samples is based on the one or more features and their predefined values corresponding to each handwashing sample derived from motion recognition technologies such as accelerometer, gyroscope, magnetometer and camera. In an embodiment of the present invention, the thresholds for various categories are automatically generated and are subject to variation based on a specific user population sample as required. Further, the handwashing samples of each category are processed to determine category features such as, minimum, maximum, median, mode, standard deviation, kurtosis, frequency domain features and any other statistical feature and corresponding values. The threshold values for determining compliance and non-compliance to hand hygiene guidelines are then generated based on the determined category features and corresponding values. Further, the threshold logic or business rules scheme for determining compliance or non-compliance to hand hygiene guidelines is based on, but not limited to, one or more statistical features, learning and pattern evaluation techniques or a combination thereof. In an embodiment of the present invention, the controller 108 is capable of, but not limited to, measuring time duration, characterizing hand movements, characterizing energy employed during handwashing and evaluating patterns to cover large demographics and physiology using handwashing samples and generating and storing the resultant data for comparison post deployment. In an embodiment of the present invention, the controller 108 may use one or more signal processing techniques, statistical techniques, neural network algorithms and machine learning and artificial intelligence techniques or any combinations thereof to ensure accurate monitoring of the handwashing instances and compliance to the hand hygiene guidelines.

Once the one or more controllers 108 are trained, the system 100 is deployed for monitoring handwashing instances in real-time. The one or more controllers 108 are configured to generate one or more compliance results for each of the one or more monitored handwashing instances by the one or more identified individuals. During operation, the data from the one or more motion sensing and recognition technologies such as, but not limited to, the accelerometer, the gyroscope and the magnetometer is processed and categorized based on, but not limited to, the root mean square values and energy computations and then compared with the threshold values (determined during training phase) for compliance and non-compliance. Based on the comparison, the one or more controllers 108 generate the one or more compliance results for each of the one or more monitored handwashing instances.

The one or more controllers 108 initiate one or more actions corresponding to each of the one or more monitored handwashing instances based on the one or more generated compliance results. In an embodiment of the present invention, the one or more actions are initiated by the one or more controllers 108 either locally or remotely using pre-stored and configurable process workflows. Further, the one or more actions initiated by the one or more controllers 108 include, but not limited to, sending the one or more generated compliance results to at least one of: the one or more user devices 104, the one or more dispensers 106, the platform 110, the server 112, the web application 114, the edge computing platform, the fog computing platform and the IoT platform. In an embodiment of the present invention, the generated compliance results are provided in the form of, but not limited to, haptic, audio and visual notifications optionally coupled with, but not limited to, numerical and real-time graph data to the one or more identified individuals. In case of non-compliance to the hand hygiene guidelines by the one or more identified individuals during a particular handwashing instance, the system 100 is capable of notifying the one or more individuals to rectify the motion pattern while the hand washing process/instance is in progress by generating recommendations and/or re-monitoring another handwashing instance.

The controller 108 is also configured to alert the one or more identified individuals to wash their hands based on, but not limited to, time elapsed since last monitored handwashing instance, proximity zone, predefined time interval and any other suitable application requirement. In an exemplary embodiment of the present invention, when the system 100 is deployed in a hospital, the controller 108 is configured to track and notify the individual such as, but not limited to, a guest or a healthcare worker to wash their hands after attending to the patient and/or on exiting the patient room in the manner described in the above sections of the specification.

In an embodiment of the present invention, once the monitoring of a handwashing instance is complete, the generated compliance results and details of the corresponding one or more actions initiated by the controller 108 are forwarded to the server 112 via the platform 110. The platform 110 and the server 112 are individually or in combination configured to store the data received from the one or more controllers 108. Further, the platform 110 and the server 112 are individually or in combination configured to process, analyze and report the received data to relevant stakeholders in a meaningful format such as, but not limited to, spreadsheets, reports, diagrams, charts, alerts and notifications. In an embodiment of the present invention, the platform 110 and server 112 are individually or in combination configured to generate one or more compliance reports and one or more recommendation reports. In an exemplary embodiment of the present invention, the platform 110 is a commercial or open-source/proprietary/in-house developed IoT platform such as, but not limited to, Carriot, AWS IoT, Microsoft Azure IoT, Google Cloud platform, ThingWorx, IBM Watson, Artik. In an embodiment of the present invention, the platform 110 is an Internet of Things (IoT) based platform such as, but not limited to, GE Predix, PTC Thingworx, Amazon Web Services (AWS) and Microsoft Azure. In an embodiment of the present invention, the server 112 is a web server with, but not limited to, Apache Tomcat, Microsoft Internet Information Services (IIS) and Nginx web server.

In an embodiment of the present invention, the system 100 may comprise an IoT platform, an edge computing platform and a fog computing platform along with the server 112. In another embodiment of the present invention, an edge computing platform is used for implementing required functionalities of the platform 110 and server 112. In yet another embodiment of the present invention, a fog computing platform is used for implementing required functionalities of the platform 110 and server 112. In yet another embodiment of the present invention, an IoT platform is used for implementing functionalities of the server 112. In yet another embodiment of the present invention, all or some of the aforementioned platforms are used with or without the server 112 for carrying out the functions of the server 112.

The server 112 is accessible to one or more users via the web application 114. The web application 114 provides a user interface which is rendered on one or more electronic communication devices of the one or more users. The one or more electronic communication devices include, but not limited to, mobile phones, tablets, laptops and desktops. In an exemplary embodiment of the present invention, the one or more users include, but not limited to, one or more employees, one or more supervisors/managers/compliance officer/administration officers in hospitals, pharmaceutical setups, cafeterias, restaurants, schools, etc. In an embodiment of the present invention, data communication and user interaction associated with the system 100 and its components is secured using standard and proprietary solutions such as, but not limited to, encryption, public/private keys, token passing, one time passwords, registration and authentication mechanisms.

In an embodiment of the present invention, the web application 114 provides options to the one or more users to filter the compliance results based on various criteria such as, but not limited to, workplace, time duration, zone, room and designation. The web application 114 also provides options to the one or more users to view summary and detailed compliance results, recommendations, view detailed compliance results corresponding to each individual/group and view detailed compliance/non-compliance results corresponding to each handwashing instance. In an embodiment of the present invention, the generated compliance results and corresponding data can be stored and analytics such as, but not limited to, descriptive, diagnostic, predictive, spatial and prescriptive can be performed to generate insights. The generated insights may comprise information such as, but not limited to, most and least non-compliant individuals, gamification, dispenser and controller diagnostics, dispenser refilling prediction, most and least compliant zones and places and the likes. In an embodiment of the present invention, the compliance results and corresponding data (such as, but not limited to, alerts, notifications, features etc.) are presented, stored and communicated to the one or more user devices, the one or more controllers, the IoT platform and the web server. In another embodiment of the present invention, the compliance results and corresponding data is published in a social network/platform using an approval mechanism/process built-in applications on computing system/processor.

In an embodiment of the present invention, any application and user dashboard associated with the system 100 such as, but not limited to, the hand hygiene application, the web application and mobile application may be personalized and customized based on their user or role of the user.

The system 100 is capable of employing any suitable wired or wireless communication mechanisms for interaction between its various components. In an embodiment of the present invention, the system 100 comprises a gamification module that facilitates providing gamification elements such as, but not limited to, individual scores, leaderboards, rankings, incentive models and compliance percentages to promote hand hygiene amongst individuals, for training and motivating the individuals with incentives for compliance and to penalize for non-compliance using the compliance results. In an embodiment of the present invention, the system 100 comprise radiation level detection sensor on the wearable device that is capable of sounding an alarm whenever the one or more individual enters a radiography or radioactive area. In an embodiment of the present invention, the wearable device comprises a biological and chemical sensor capable of monitoring environment around the one or more individuals. In an embodiment of the present invention, the wearable device comprises a microphone capable of capturing conversations such as a doctor's consultation and prescription and converting the same into a written report using Natural Language Processing (NLP) techniques such as, but not limited to, Latent Dirichlet Allocation and deep learning techniques. In an embodiment of the present invention, the wearable device is initially trained for an individual using handwashing samples of the individual. Further, the handwashing samples may reside on at least one of: the wearable device, the controller 108, the platform 110 and the server 112.

In an embodiment of the present invention, the one or more controllers communicate with the server 112 directly without any intermediary or the platform 110. In another embodiment of the present invention, inbuilt sensing, processing, communication and computing components of the one or more user devices 104 are used as the controller 108 without the need of a separate controller. In yet another embodiment of the present invention, the one or more controllers are edge devices. In yet another embodiment of the present invention, the one or more controllers 108 communicate with one or more edge devices for performing its functions.

Figure 2:
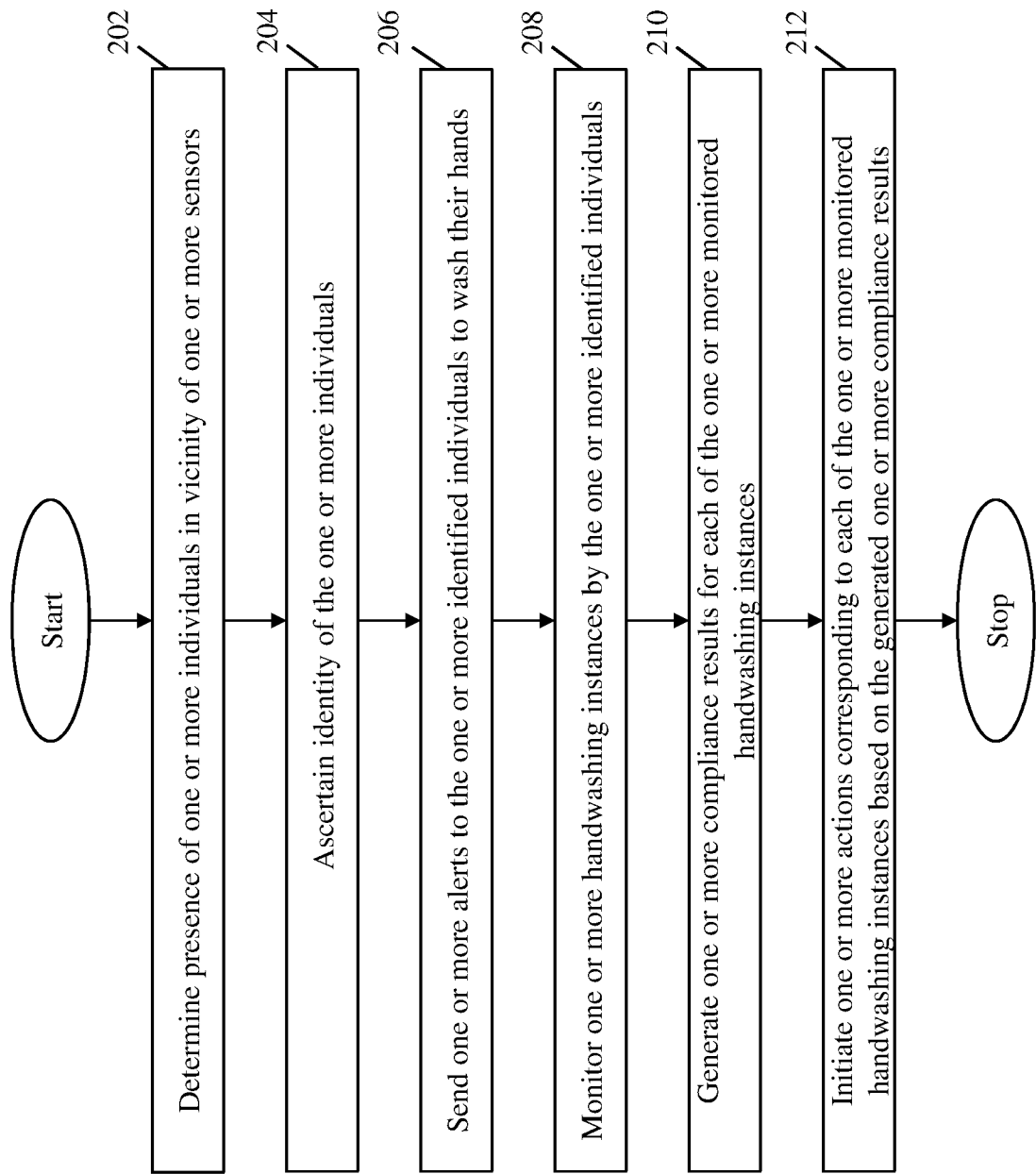
FIG. 2 is a flowchart illustrating a method for efficiently monitoring hand hygiene, in accordance with an embodiment of the present invention.

FIG. 2 is a flowchart illustrating a method for efficiently monitoring hand hygiene, in accordance with an embodiment of the present invention.

At step 202, presence of one or more individuals in vicinity of one or more sensors is determined. The one or more sensors include, but not limited to, cameras, beacons, Radio-Frequency Identification (RFID) readers, proximity sensors, movement sensors, audio sensors, light sensors, activity sensors, motion sensors and olfactory sensors. Further, the one or more sensors employ technologies such as, but not limited to, Bluetooth, Infrared and Zigbee. In an embodiment of the present invention, the one or more sensors are mounted at entry/exit or at any suitable location as per the requirements of various pre-defined zones within a pre-defined region such as, but not limited to, a healthcare facility, a kitchen, a restaurant, a food packaging unit, a food processing unit, a school, a cafeteria, a house and any other region that requires monitoring of hand hygiene of the one or more individuals. In an exemplary embodiment of the present invention, the one or more sensors are mounted on doors of the patient rooms in a hospital. In an embodiment of the present invention, the one or more individuals include, but not limited to, guests, hospital personnel, food processing workers, cooking staff, school staff, restroom workers and users, pharmaceutical room cleaning workers and any person within the pre-defined region.

In an embodiment of the present invention, the one or more sensors determine presence of the one or more individuals by tracking one or more user devices of the one or more individuals. In an embodiment of the present invention, Received Signal Strength Indicator (RSSI) values received from the one or more user devices are used to determine presence of the one or more individuals. The one or more user devices are electronic communication devices such as, but not limited to, mobile phones, tablets and wearable devices. In an embodiment of the present invention, the wearable devices include, but not limited to, smart watches, smart glasses, smart bands and fitness bands. In an embodiment of the present invention, the one or more user devices are specially designed proprietary or Commercial-Off-The-Shelf (COTS) wearable devices worn by the one or more individuals for hand hygiene monitoring. In an embodiment of the present invention, the one or more user devices include, but not limited to, an RFID tag which is tracked by the RFID reader to determine presence of the individual in the vicinity of the RFID reader. In an embodiment of the present invention, the one or more user devices comprise motion sensing technologies such as, but not limited to, gyroscope, accelerometer, magnetometer and camera that facilitate in determining hand washing patterns of the individuals for monitoring hand hygiene.

At step 204, identity of the one or more individuals is ascertained. In an embodiment of the present invention, on determining presence of the one or more individuals, the one or more sensors ascertain identity of the one or more individuals using the one or more user devices present in the vicinity of the one or more sensors that belong to the one or more individuals. In another embodiment of the present invention, the one or more sensors generate one or more triggers that facilitate in ascertaining the identity of the one or more individuals. Further, the one or more triggers comprise identification data such as, but not limited to, device ID, serial number, user name, device name, user ID, registration ID. The identification data is matched with a pre-stored list of user devices and corresponding pre-stored identification data, present in a database of registered user devices belonging to various individuals, to ascertain the identity of the individual/user device. In another embodiment of the present invention, the identification data is used for automatic registration at run time in case of absence of corresponding pre-stored identification data. In an embodiment of the present invention, the identification data is gathered through an online or an offline registration process and/or updated with application settings either locally or remotely.

In an embodiment of the present invention, determination of identity of the individual/user device may happen locally at, but not limited to, the one or more sensors, the one or more user devices, one or more proprietary or third party devices, one or more gateways, one or more processors and one or more servers, one or more computing platforms and/or combinations thereof with suitable security measures.

In an embodiment of the present invention, determination of identity of the individual/user device may happen globally at, but not limited to, an IoT platform, a cloud platform, an edge computing platform, a fog computing platform, a server and/or a combination thereof. The determination of the identity of the individual/user device may involve security measures such as, but not limited to, token passing and usage of public/private keys.

At step 206, one or more alerts are sent to the one or more identified individuals to wash their hands. In an embodiment of the present invention, the one or more alerts are sent to at least one of: the one or more user devices belonging to the one or more individuals and to the server for storing as one or more log files or in a suitable format within a database. Further, a hand hygiene application is installed on the one or more user devices which receives the one or more alerts. In an embodiment of the present invention, the wearable device of the individual receives the one or more alerts and provides notifications in the form of, but not limited to, haptic motion, audio and visual notifications to alert the individual to wash his/her hands.

In an embodiment of the present invention, the one or more sensors are mounted on one or more dispensers. In an embodiment of the present invention, the one or more dispensers are electronic devices used for dispensing hand wash product and capable of communicating with the one or more sensors, the one or more user devices and the one or more servers. Further, the one or more dispensers are configured to receive the one or more alerts. On receiving the one or more alerts, a light on the one or more dispensers is turned on or starts blinking to alert/notify the one or more individuals in the vicinity of the one or more sensors or the one or more dispensers to wash their hands. In another embodiment of the present invention, the one or more dispensers initiate an audio alert or visual alert and automatically dispense the hand washing product if the one or more individuals are standing near the dispenser. In case the one or more individuals are away from the dispenser then the one or more individuals are notified to wash their hands. In yet another embodiment of the present invention, the dispenser is capable of performing functionalities of the sensor as well. In an embodiment of the present invention, the one or more sensors may be stationary or movable or installed on a movable platform. In an embodiment of the present invention, the movable platform is a robot.

At step 208, one or more handwashing instances by the one or more identified individuals are monitored. In an embodiment of the present invention, the one or more dispensers using a pre-installed camera take a picture or video, record and monitor one or more hand washing instances by the one or more identified individuals. Further, the camera can also be used for identifying the person using face recognition prior to monitoring hand washing. In another embodiment of the present invention, the one or more dispensers record and monitor the one or more handwashing instances using one or more motion recognition technologies such as, but not limited to, an accelerometer, a gyroscope and a magnetometer. In yet another embodiment of the present invention, on receiving the one or more alerts to wash their hands, the one or more individuals access the hand hygiene application on their mobile phone or personal computing device or Personal Digital Assistant (PDA) or wearable device which then monitors the one or more hand washing instances by the one or more identified individuals. In yet another embodiment of the present invention, the one or more handwashing instances are monitored by the motion sensing technologies such as, but not limited to, accelerometer, the gyroscope and the magnetometer residing on the wearable device worn by the one or more identified individuals.

At step 210, one or more compliance results for each of the one or more monitored handwashing instances are generated. The one or more compliance results include, but not limited to, information which indicates whether the one or more identified individuals complied with hand washing guidelines during the one or more handwashing instances. The handwashing guidelines are a set of minimum requirements with respect to, but not limited to, pattern, sequence, timing (which includes total and atomic for sub patterns) and energy used during washing for complete hand hygiene. Further, the handwashing guidelines are configurable and pre-defined. Furthermore, the handwashing guidelines are defined and configured based on requirement of the application.

In an embodiment of the present invention, a sensing and computing application which uses a combination of various algorithms and techniques such as, but not limited to, time-series pattern matching and event detection algorithms, Dynamic Time Warping (DTW) algorithms, different distance metrics, clustering and correlation techniques and spectral techniques such as discrete Fourier transform are used for energy computation and classifying patterns into different categories or buckets thereby determining if the one or more identified individuals complied with the hand hygiene guidelines during the one or more monitored handwashing instances.

Various handwashing samples are used for training in order to determine compliance to hand hygiene guidelines. In an embodiment of the present invention, any suitable platform such as, but not limited to, edge computing, fog computing, cloud computing is used for training prior to deployment and/or training at run time. In another embodiment of the present invention, different self-learning techniques or human driven training algorithms are used for training. The handwashing samples include different types of handwashing patterns and sequences that either comply or do not comply with the handwashing guidelines. In an embodiment of the present invention, the samples used for training include, but not limited to, handwashing patterns adhering to World Health Organization (WHO) hand hygiene guidelines or any other guidelines or a combination thereof. In an embodiment of the present invention, the handwashing samples are categorized into predefined categories or buckets such as, but not limited to, vigorous, normal and slow based on predefined threshold values of one or more features such as, but not limited to, energy and root mean square. Further, categorization of the handwashing samples is based on the one or more features and their predefined values corresponding to each handwashing sample derived from motion recognition technologies such as the accelerometer, the gyroscope and the magnetometer. In an embodiment of the present invention, the thresholds for various categories are automatically generated and are subject to variation based on a specific user population sample. Further, the handwashing samples of each category are processed to determine category features such as, minimum, maximum, median, mode, standard deviation, kurtosis, frequency domain features and any other statistical feature and corresponding values. The threshold values for determining compliance and non-compliance to hand hygiene guidelines are then generated based on the determined category features and corresponding values. Further, the threshold logic or business rules scheme for determining compliance or non-compliance to hand hygiene guidelines is based on one or more learning, statistical and pattern evaluation and artificial intelligence techniques or a combination thereof.

Once the training phase is complete, handwashing instances are monitored in real-time using the one or more motion sensing and recognition techniques. The values generated corresponding to the handwashing instances are compared with pre-stored threshold values corresponding to various categories for determining compliance and non-compliance to hand hygiene guidelines and generating compliance results. In an embodiment of the present invention, one or more proprietary feature extraction algorithms, one or more thresholds, one or more neural network algorithms and machine learning, statistical and artificial intelligence techniques or combination thereof are used to ensure accurate monitoring of the handwashing instances and compliance to the hand hygiene guidelines.

During operation, the data from the one or more motion sensing and recognition technologies such as, but not limited to, the accelerometer, the gyroscope and the magnetometer is processed and categorized based on features such as, but not limited to, the root mean square values and energy computations and then compared with the threshold values (determined during training phase) for compliance and non-compliance. Based on the comparison, the one or more compliance results are generated for each of the one or more monitored handwashing instances. In an embodiment of the present invention, compliance results also comprise data related to washing liquid and chemical levels, dispenser condition and status of sensors and controllers.

At step 212, one or more actions corresponding to each of the one or more monitored handwashing instances are initiated based on the generated one or more compliance results. Further, the one or more actions are initiated either locally or remotely using pre-stored and configurable process workflows. Furthermore, the one or more initiated actions include, but not limited to, sending the generated compliance results to at least one of: the one or more user devices, the one or more dispensers, the cloud platform, the server, the web application, the edge computing platform, the fog computing platform and the IoT platform. In an embodiment of the present invention, the generated compliance results are provided in the form of, but not limited to, haptic notifications, audio notifications, visual notifications and one or more reports or any combinations thereof to the one or more identified individuals. In case of non-compliance to the hand hygiene guidelines by the one or more identified individuals during a particular handwashing instance, the one or more individuals are either notified to rectify the motion pattern while the hand washing process/instance is in progress by providing real-time recommendations and/or are notified to restart hand washing which is then monitored as a new handwashing instance.

In an embodiment of the present invention, the compliance results are analyzed to generate insights comprising information related to most and least non-compliant individuals, gamification, dispenser and controller diagnostics, dispenser refilling prediction, most and least compliant zones and places.

Figure 3:
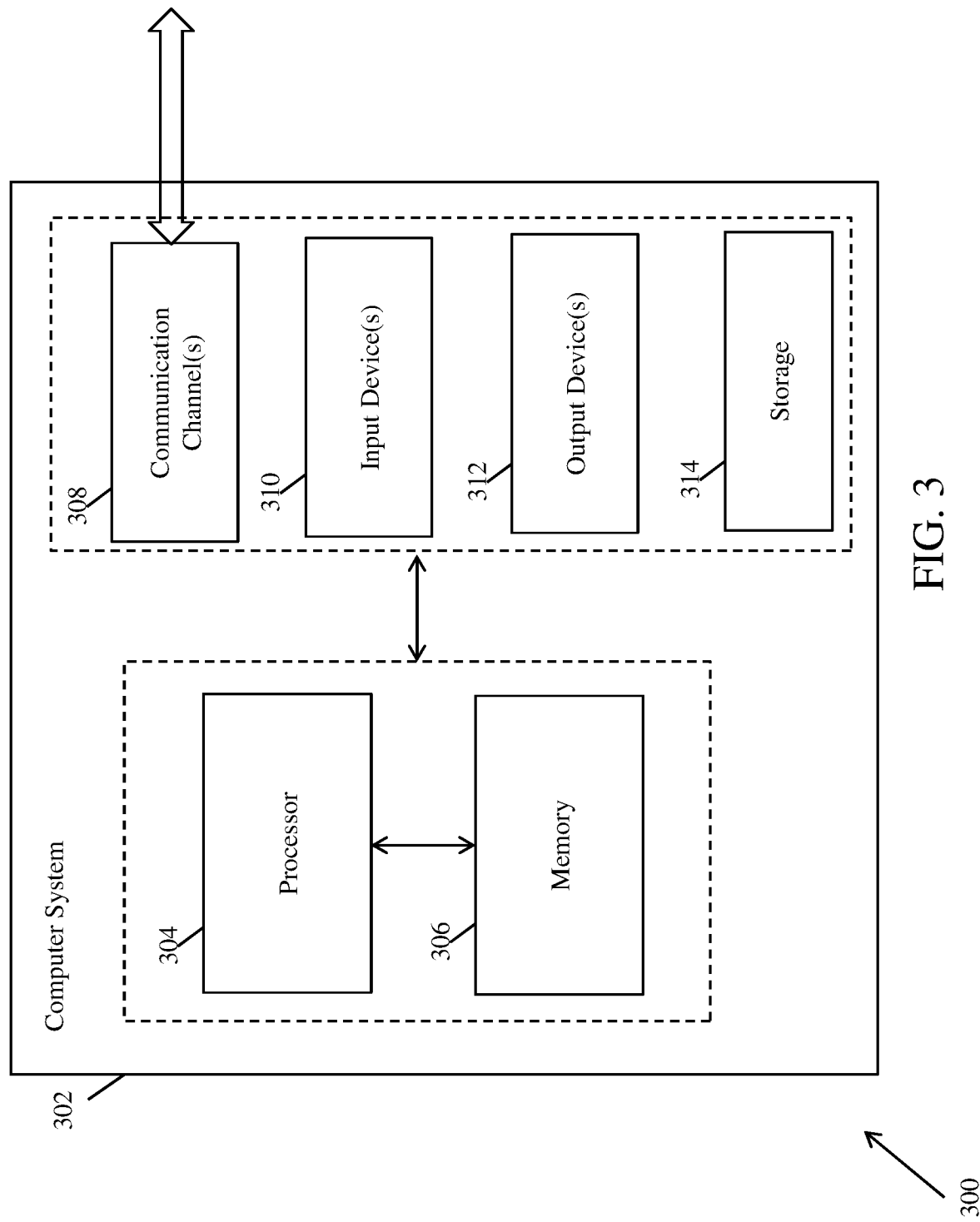
FIG. 3 illustrates an exemplary computer system for efficiently monitoring hand hygiene, in accordance with an embodiment of the present invention.

FIG. 3 illustrates an exemplary computer system for efficiently monitoring hand hygiene, in accordance with an embodiment of the present invention.

The computer system 302 comprises a processor 304 and a memory 306. The processor 304 executes program instructions and may be a real processor. The processor 304 may also be a virtual processor, a remote processor or a combination of different computing elements. The computer system 302 is not intended to suggest any limitation as to scope of use or functionality of described embodiments. For example, the computer system 302 may include, but not limited to, a general-purpose computer, a programmed microprocessor, a micro-controller, a peripheral integrated circuit element, and other devices or arrangements of devices that are capable of implementing the steps that constitute the method of the present invention. In an embodiment of the present invention, the memory 306 may store data, settings and software for implementing various embodiments of the present invention. The computer system 302 may have additional components. For example, the computer system 302 includes one or more communication channels 308, one or more input devices 310, one or more output devices 312, and storage 314. An interconnection mechanism (not shown) such as a bus, controller, or network, interconnects the components of the computer system 302. In various embodiments of the present invention, operating system software (not shown) provides an operating environment for various softwares executing in the computer system 302, and manages different functionalities of the components of the computer system 302. In various embodiments of the present invention, the computer system 302 comprise a virtual machine and/or virtualization and orchestration layers if required. The computer system 302 may also connect to different input and output devices such as, but not limited to, sensors, actuators and data communication/notification mechanisms.

The communication channel(s) 308 allow communication over a communication medium to various other computing entities. The communication medium provides information such as program instructions, or other data in a communication media. The communication media includes, but not limited to, wired or wireless methodologies implemented with an electrical, optical, RF, infrared, acoustic, microwave, bluetooth or other transmission media.

The input device(s) 310 may include, but not limited to, a keyboard, mouse, pen, joystick, trackball, a voice device, a scanning device, or any another device that is capable of providing input to the computer system 302. In an embodiment of the present invention, the input device(s) 310 may be a sound card or similar device that accepts audio input in analog or digital form. In an embodiment of the present invention, the input device(s) 310 may be a touch sensor, a proximity/gesture sensor or a similar device. The output device(s) 312 may include, but not limited to, a user interface on CRT or LCD, printer, speaker, CD/DVD writer, or any other device that provides output from the computer system 302.

The storage 314 may include, but not limited to, magnetic disks, magnetic tapes, CD-ROMs, CD-RWs, DVDs, SSD, USB disc, memory card, flash drives or any other medium which can be used to store information and can be accessed by the computer system 302. In various embodiments of the present invention, the storage 314 contains program instructions for implementing the described embodiments.

The present invention may suitably be embodied as a computer program product for use with the computer system 302. The method described herein is typically implemented as a computer program product, comprising a set of program instructions which is executed by the computer system 302 or any other similar device. The set of program instructions may be a series of computer readable codes stored on a tangible medium, such as a computer readable storage medium (storage 314), for example, diskette, CD-ROM, ROM, flash drives or hard disk, or transmittable to the computer system 302, via a modem or other interface device, over either a tangible medium, including but not limited to optical or analogue communications channel(s) 308. The implementation of the invention as a computer program product may be in an intangible form using wireless techniques, including but not limited to microwave, infrared, bluetooth or other transmission techniques. These instructions can be preloaded into a system or recorded on a storage medium such as a CD-ROM, or made available for downloading over a network such as the internet or a mobile telephone network or as an Over The Air (OTA) update. The series of computer readable instructions may embody all or part of the functionality previously described herein.

The present invention may be implemented in numerous ways including as an apparatus, method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

We claim:

1. A system for efficiently monitoring hand hygiene, the system comprising:
one or more sensors configured to determine presence of one or more individuals in vicinity; and
a processor configured to execute instructions stored in a memory and configured to:
ascertain identity of the one or more individuals;
send one or more alerts to the one or more identified individuals to wash their hands;
monitor one or more handwashing instances by the one or more identified individuals;
generate one or more compliance results for each of the one or more monitored handwashing instances, wherein the one or more compliance results comprise information which indicates whether the one or more identified individuals complied with handwashing guidelines comprising a set of minimum requirements with respect to pattern, sequence, timing and energy used during washing for complete hand hygiene and wherein the handwashing guidelines are configurable based on requirement;

initiate one or more actions corresponding to each of the one or more monitored handwashing instances based on the generated one or more compliance results, wherein the compliance results comprise data related to washing liquid and chemical levels, dispenser condition and status of sensors and controllers, and wherein the one or more compliance results are analyzed to generate insights comprising information related to least and most non-compliant individuals, gamification, dispenser and controller diagnostics, dispenser refilling prediction and most and least compliant zones and places; and provide gamification elements comprising individual scores, leaderboards, rankings, incentive models and compliance percentages using the one or more compliance results.

2. The system of claim 1, wherein the one or more sensors comprise cameras, beacons, Radio-Frequency Identification (RFID) readers, proximity sensors, movement sensors, audio sensors, light sensors, activity sensors, motion sensors and olfactory sensors.

3. The system of claim 1, wherein the presence of the one or more individuals in vicinity of the one or more sensors is determined by tracking one or more user devices of the one or more individuals.

4. The system of claim 3, wherein the one or more user devices are electronic communication devices comprising mobile phones, tablets and wearable devices.

5. The system of claim 1, wherein the one or more alerts are notifications comprising a haptic motion, an audio notification and a visual notification.

6. The system of claim 1, wherein the one or more handwashing instances are monitored using one or more motion sensing technologies comprising an accelerometer, a gyroscope, a magnetometer and a camera.

7. The system of claim 1, wherein the one or more compliance results comprise information which indicates whether the one or more identified individuals complied with the handwashing guidelines during the one or more handwashing instances.

8. The system of claim 1, wherein the one or more actions corresponding to each of the one or more monitored handwashing instances comprise sending the one or more generated compliance results to at least one of: one or more user devices, one or more dispensers, a cloud platform, a server, a web application, an edge computing platform, a fog computing platform and an Internet of Things (IoT) platform.

9. A computer-implemented method for efficiently monitoring hand hygiene, via program instructions stored in a memory and executed by a processor, the computer-implemented method comprising:

determining presence of one or more individuals in vicinity of one or more sensors;

ascertaining identity of the one or more individuals;

sending one or more alerts to the one or more identified individuals to wash their hands;

monitoring one or more handwashing instances by the one or more identified individuals;

generating one or more compliance results for each of the one or more monitored handwashing instances, wherein the one or more compliance results comprise information which indicates whether the one or more identified individuals complied with handwashing guidelines comprising a set of minimum requirements with respect to pattern, sequence, timing and energy used during washing for complete hand hygiene and wherein the handwashing guidelines are configurable based on requirement;

initiating one or more actions corresponding to each of the one or more monitored handwashing instances based on the generated one or more compliance results, wherein the compliance results comprise data related to washing liquid and chemical levels, dispenser condition and status of sensors and controllers, and wherein the one or more compliance results are analyzed to generate insights comprising information related to least and most non-compliant individuals, gamification, dispenser and controller diagnostics, dispenser refilling prediction and most and least compliant zones and places; and providing gamification elements, wherein gamification elements comprises individual scores, leaderboards, rankings, incentive models and compliance percentages using the one or more compliance results.

10. The computer-implemented method of claim 9, wherein the one or more sensors comprise cameras, beacons, Radio-Frequency Identification (RFID) readers, proximity sensors, movement sensors, audio sensors, light sensors, activity sensors, motion sensors and olfactory sensors.

11. The computer-implemented method of claim 9, wherein the presence of the one or more individuals in vicinity of the one or more sensors is determined by tracking one or more user devices of the one or more individuals.

12. The computer-implemented method of claim 11, wherein the one or more user devices are electronic communication devices comprising mobile phones, tablets and wearable devices.

13. The computer-implemented method of claim 9, wherein the one or more alerts are notifications comprising a haptic motion, an audio notification and a visual notification.

14. The computer-implemented method of claim 9, wherein the one or more handwashing instances are monitored using one or more motion sensing technologies comprising an accelerometer, a gyroscope, a magnetometer and a camera.

15. The computer-implemented method of claim 9, wherein the one or more compliance results comprise information which indicates whether the one or more identified individuals complied with the handwashing guidelines during the one or more handwashing instances.

16. The computer-implemented method of claim 9, wherein the one or more actions corresponding to each of the one or more monitored handwashing instances comprise sending the one or more generated compliance results to at least one of: one or more user devices, one or more dispensers, a cloud platform, a server, a web application, an edge computing platform, a fog computing platform and an Internet of Things (IoT) platform.

* * * * *